United States Patent [19]

Sekine et al.

[11] Patent Number: 4,854,691

[45] Date of Patent: Aug. 8, 1989

[54] LASER BEAM SCANNING TYPE EYE FUNDUS CAMERA

[75] Inventors: Akihiko Sekine; Shinji Wada; Takashi Yokokura; Kazuo Nunokawa; Masayuki Hideshima, all of Tokyo, Japan

[73] Assignee: Tokyo Kogaku Kikai Kabushiki Kaisha, Tokyo, Japan

[21] Appl. No.: 199,716

[22] Filed: May 27, 1988

[30] Foreign Application Priority Data

May 27, 1987 [JP] Japan .................................. 62-130832

[51] Int. Cl.4 .............................................. A61B 3/10
[52] U.S. Cl. .................................................. 351/221
[58] Field of Search ............... 351/206, 221; 128/665, 128/395, 303.1

[56] References Cited

U.S. PATENT DOCUMENTS 4,393,366  7/1983  Hill ...................................... 351/221

Primary Examiner—Rodney B. Bovernick
Assistant Examiner—P. M. Dzierzynski
Attorney, Agent, or Firm—Finnegan, Henderson, Farabow, Garrett & Dunner

[57] ABSTRACT

A laser beam scanning type eye fundus camera has a laser beam generator for generating a laser beam; an illuminating system for illuminating the fundus of an eye to be tested by scanning the laser beam generated by the laser beam generator on the eye fundus; a first and a second light receiving portions for receiving a reflecting light of the laser beam reflected by the eye fundus; a first light receiving system for guiding the reflecting light of the laser beam reflected by the eye fundus to the first light receiving portion; a second light receiving system for guiding a fluorescence excited at the eye fundus by the laser beam; and an electronic circuit for forming an eye fundus image on a monitor TV according to an output signal coming from the first and second light receiving portions.

15 Claims, 5 Drawing Sheets

LASER BEAM SCANNING TYPE EYE FUNDUS CAMERA

BACKGROUND OF THE INVENTION

1. Field of the Invention

This invention relates to a laser beam scanning type eye fundus camera, in which the fundus of an eye to be tested is illuminated by scanning a laser beam.

2. Description of the Prior Art

Currently, there are two ways of observing and taking a picture of an eye fundus using an eye fundus camera; one is that the picture of an eye fundus is observed and taken by the ordinary procedure using visible rays (hereinafter simply referred to as "ordinary method"), and the other is that the picture of an eye fundus is observed and taken by fluorescence (hereinafter simply referred to as "fluorescence method" or "picture-taking by fluorescence").

When a picture of the eye fundus is to be taken by using light of a wavelength for exciting the fluorescent agent to generate fluorescence, a person to be tested usually gets an injection of a fluorescent agent into his arm vein, for example, and the injected fluorescent agent is circulated through the blood vessel of his eye fundus. On the other hand, the eye fundus camera usually irradiates light of a wavelength for exciting the fluorescent agent to generate fluorescence toward the eye fundus so that fluorescence is emitted at the blood vessel portion of the eye fundus, and a filter for the use of fluorescence is inserted into an optical path of an observation picture-taking optical system in order to cut a reflecting light of a wavelength other than the fluorescence.

In general, when a fluorescent agent is injected into the arm vein of a person to be tested, it usually takes about 5 to 10 seconds before the fluorescence starts its circulation in the blood vessel of his eye fundus, and it takes some more time until the fluorescence will have been fully circulated in the blood vessel of his eye fundus. Therefore, the inspector can know the state of the blood vessel of the eye fundus by observing and taking a picture of any change of the blood vessel of the eye fundus with the passage of time by fluorescence. However, since the change of the blood vessel of the eye fundus by the fluorescence is comparatively short in period of time from when the change of the eye fundus is first taken place until when it is stabilized, the picture taking operation is usually started immediately before the appearance of the blood vessel of the eye fundus by the fluorescence.

On the other hand, when the blood vessel of the eye fundus is to be observed and taken a picture by fluorescence, the eye fundus camera is naturally required to be well focussed on the eye fundus. Moreover, since the eye fundus is not constant and is easy to move, the focus must be adjusted frequently during the fluorescent observation picture-taking.

However, it occurs that the eye fundus is not seen at all in the early stage of the picture-taking operation of the blood vessel by fluorescence because the fluorescent filter is located in the optical path as described. Furthermore, the production rate of the fluorescence is very small at the blood vessel of the eye fundus in the early stage of the appearance of the blood vessel. Therefore, in the foregoing state, much difficulty is experienced in adjusting the focus of the eye fundus camera. Because of the foregoing reasons, it is desirable that the focus of the eye fundus camera can be adjusted by observing the object under the ordinary light or visible rays when the blood vessel of the eye fundus is to be taken a picture by fluorescence. However, the problem is that under such circumstance as that a filter for the use of fluorescence is disposed in the optical path as described, the eye fundus camera is practically impossible to be well focussed under the ordinary light.

Furthermore, the positional relationship between the blood vessel and the remaining portion of the eye fundus is difficult to obtain accurately only by the fluorescent picture-taking of the blood vessel of the eye fundus as described. Therefore, when the positional relationship is to be obtained accurately, it is recommended that the object be observed and photographed under the ordinary light and photographed under fluorescence, and both pictures taken are overlapped one upon the other for comparison.

However, when a filter for the use of fluorescence is disposed in the optical path of the conventional eye fundus camera, a picture of the blood vessel of the eye fundus can be taken only by fluorescence and a picture thereof can not be taken under the ordinary light. On the contrary, when a picture can be taken under the ordinary light, a picture taken by fluorescence can not be obtained because a filter for the use of fluorescence is not placed in the optical path of the eye fundus camera.

As a consequence, when the relationship between an image of the blood vessel of the eye fundus by fluorescence and that of the remaining portion thereof is to be obtained accurately, an observation picture-taking operation by fluorescence and an observation picture-taking operation under the ordinary light must be effected alternately.

However, since the objective eye fundus is very difficult to be kept constant, when the picture-taking by fluorescence and the picture-taking under the ordinary light are carried out alternately, a time lag occurs in two pictures taken in accordance with the afore-mentioned different procedures, i.e., between the image of the blood vessel of the eye fundus and that of the eye fundus. As a result, although it is possible to compare the image of the blood vessel of the eye fundus and that of the eye fundus by placing them side by side, it is impossible to obtain the accurate positional relationship by overlapping both the images.

SUMMARY OF THE INVENTION

The present invention aims at providing a laser beam scanning type eye fundus camera, in which the fluorescence method of photographing the blood vessel of the eye fundus and the ordinary method of photographing the eye fundus can be carried out simultaneously.

In order to achieve the above object, the present invention provides a laser beam scanning type eye fundus camera having an irradiating system for scanning a laser beam on the eye fundus of an eye to be tested and a light receiving system for introducing light from the eye fundus to a light receiving portion. The light receiving portion comprises a first light receiving portion for receiving only light of the same wavelength as the laser beam, and a second light receiving portion for receiving only light of a fluorescent wavelength generated from the blood vessel by the irradiation of the laser beam. The light from the eye fundus introduced by the light receiving system is introduced to the first and the second light receiving portions, respectively.

With the above-mentioned constitution, when the eye fundus of the person to be tested is scanned with the laser beam after the person gets an injection of a fluorescent agent, the laser beam is reflected by the eye fundus. At the same time, the laser beam is irradiated to the fluorescent agent in the blood vessel of the eye fundus and excited to emit fluorescence at the blood vessel portion of the eye fundus. And, a reflecting light of the laser beam is received by the first light receiving portion and subjected to an ordinary observation picture-taking. On the other hand, the fluorescence is received by the second light receiving portion and subjected to an observation picture-taking of the blood vessel of the eye fundus by fluorescence.

BRIEF DESCRIPTION OF THE ATTACHED DRAWINGS

Figure 1:
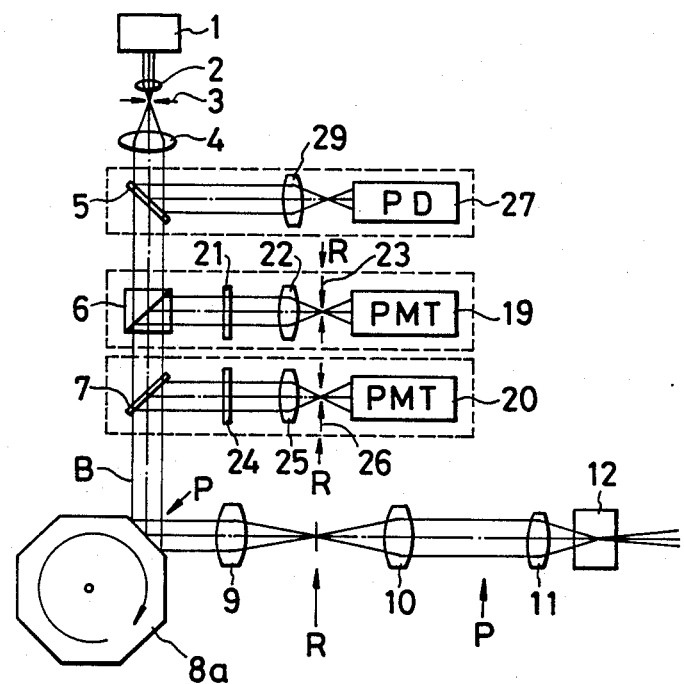
FIG. 1 is a schematic view of an optical system showing the first embodiment of a laser beam scanning type eye fundus camera according to the present invention.
Figure 2:
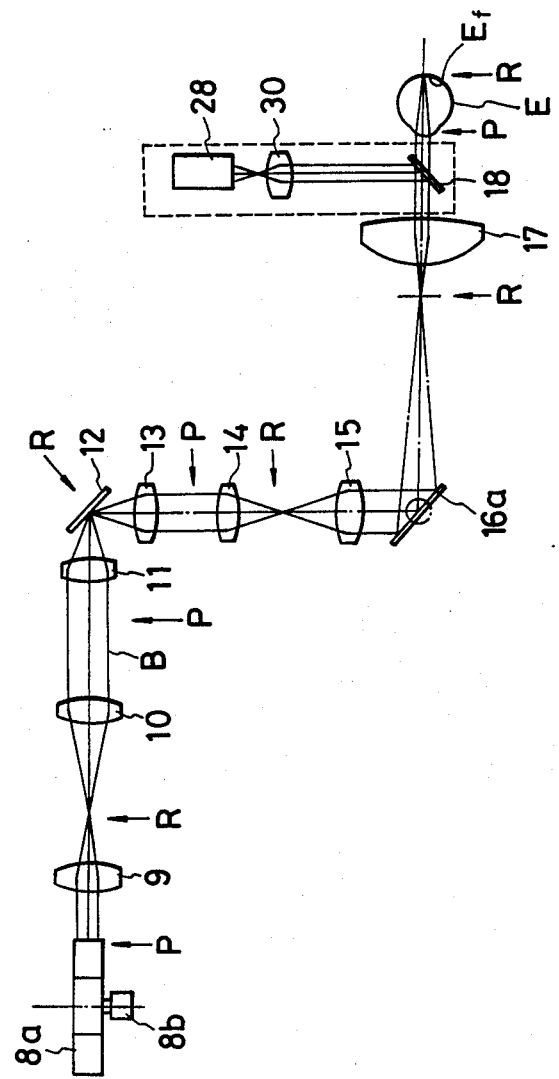
FIG. 2 is likewise a schematic view of the optical system of FIG. 1 but when viewed from a different angle.
Figure 3:
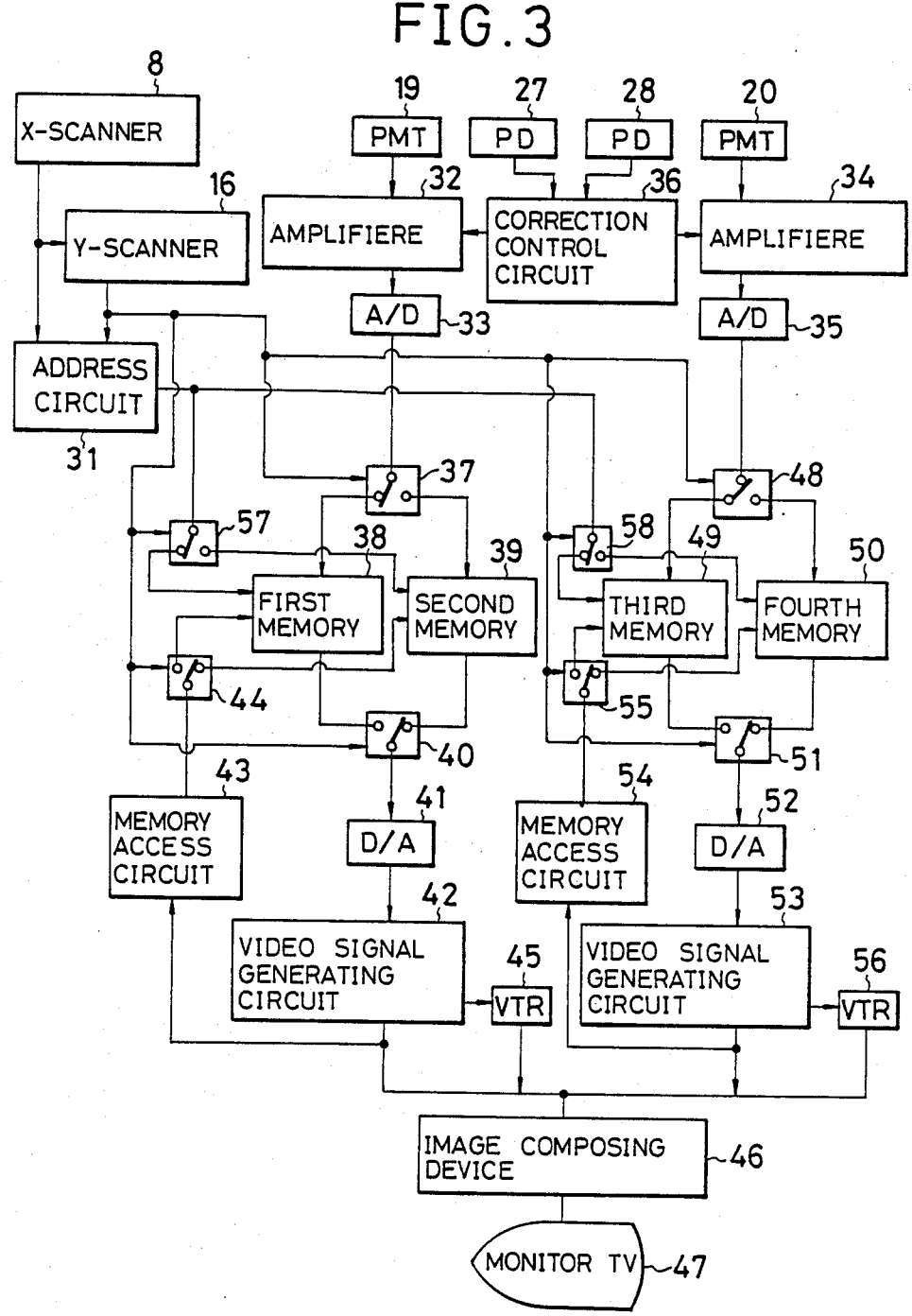
FIG. 3 is a block diagram of an electronic control system which acts in cooperation with the optical system of FIGS. 1 and 2.
Figure 4:
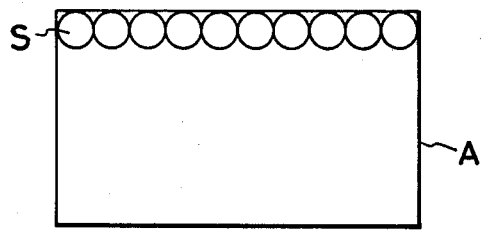
Figure 5:
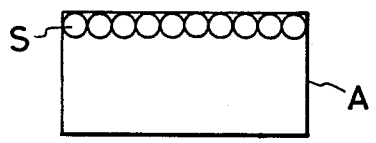
Figure 6:
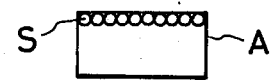
Figure 7:
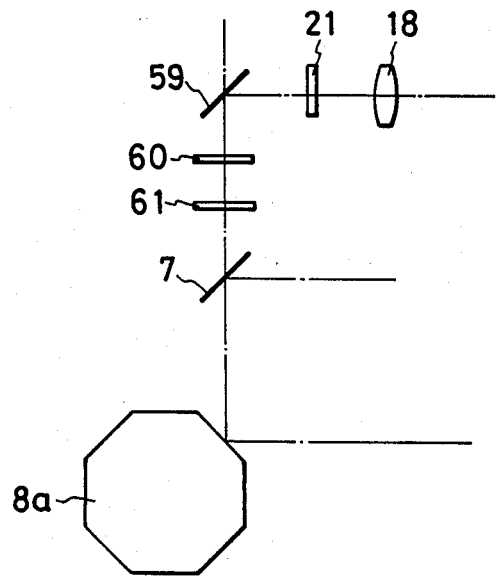
Figure 8:
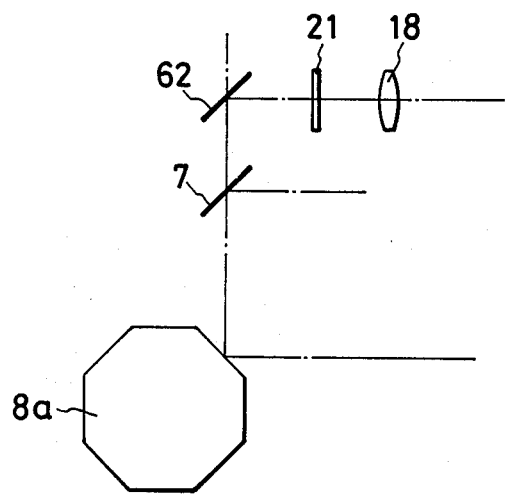

FIG. 4 through FIG. 6 are illustrations for explaining the relation between the angle of view and the diameter of the spot of the laser beam when the angle of view and the diameter of the spot of the laser beam are polarized by using a part of the optical system of FIGS. 1 and 2; and FIG. 7 and FIG. 8 are schematic views showing the second and the third embodiments of a laser beam scanning type eye fundus camera according to the present invention.

DESCRIPTION OF THE PREFERRED EMBODIMENT

FIG. 1 through FIG. 6 illustrate the first embodiment of the present invention.

An eye fundus camera shown in FIG. 1 and FIG. 2 includes a laser generator 1, an illuminating system for illuminating the eye fundus $E_f$ of an eye E to be tested by scanning a laser beam (an illuminating light) generated by the laser beam generator 1 thereon, a light receiving portion for receiving a reflecting light reflected by the eye fundus $E_f$ and light such as fluorescence excited at the blood vessel (not shown) of the eye fundus, and a light receiving system for guiding the reflecting light and the light such as fluorescence to the light receiving portion.

The laser beam generator 1 is adapted to generate a laser beam of a wavelength able to generate fluorescence by exciting a fluorescent agent, the laser beam being of 488 nm, for example.

The illuminating system comprises such optical parts as a laser beam collimating lens 2, a pin hole 3, a collimating lens 4, a half mirror 5, a polarized beam splitter 6, a dichroic mirror 7, a polygon mirror 8a of an X-scanner for a horizontal scanning (X-direction scanning), variable lenses 9, 10, a relay lens 11, a reflecting mirror 12, focus lenses 13, 14, a relay lens 15, a galvano mirror 16a of a Y-scanner 16 for a vertical scanning (Y-direction scanning), an objective lens 17, and a half mirror 18, which are arranged in this order from the laser beam generator 1 side. The dichroic mirror 7 is adapted to transmit a laser beam of 488 nm and reflect light of a wavelength of 520 nm. The variable lenses 9, 10 are adapted to change the combination of focal distance. By changing the combination of the focal distance of the variable lenses 9, 10, the angle of view of the horizontal scanning by laser beam is changed and the diameter of the spot of laser beam is changed. As a result, the scanning angle of the galvano mirror 16a is changed and the vertical scanning angle of view is also changed. In this way, the variable lenses 9, 10 and the galvano mirror 16a are linked as such that when the scanning view angle A is changed as shown in FIG. 4 through FIG. 6, the spot diameter S of a laser beam B is changed at a predetermined ratio with respect to the view angle A. Since the focus lenses 13, 14 are movably disposed in the direction of the optical axis, the change of the spot diameter due to difference of refractivity of the eye B can be maintained constant by moving the focus lenses 13, 14 in the direction of the optical axis. In the figures, P denotes a position conjugate with the pupil $E_p$ of the eye E and R denotes a position conjugate with the eye fundus $E_f$ of the eye E.

In such illuminating system, the laser beam B generated by the laser beam generator a is scanned in the X-direction by the rotation of the polygon mirror 8a after passing through the laser beam collimating lens 2, the pin hole 3, the collimating lens 4, the half mirror 5, the polarized beam splitter 6 and the dichroic mirror 7. The scanned laser beam B is varied by the variable lenses 9,10 and thereafter, scanned for illuminating the eye fundus $E_f$ of the eye E through the relay lens 11, the reflecting mirror 12, the focus lenses 13, 14, the relay lens 15, the galvano mirror 16a, the objective lens 17, the half mirror 18, etc. And, the scanning position is gradually changed in the Y-direction by turning the galvano mirror 16a at a predetermined angle every time one scanning is effected by the polygon mirror 8a.

The above-mentioned light receiving portion includes a photomultiplier 19 (the first light receiving portion) for receiving a reflecting light, i.e., light of the same wavelength as laser beam, coming from the eye fundus $E_f$, and a photomultiplier 20 (the second light receiving portion) for receiving a fluorescent wavelength coming from the blood vessel (not shown) of the eye fundus.

The above-mentioned light receiving system includes a first light receiving system for guiding a laser beam reflected by the eye fundus $E_f$ to the photomultiplier 19, and a second light receiving system for guiding fluorescence from the blood vessel of the eye fundus $E_f$ to the photomultiplier 20.

The first light receiving system uses the same optical system from the polarized beam splitter 6 to the half mirror 18 of the illuminating system and further comprises an analyzer 21, a condenser lens 22, and a pin hole 23 in addition to this optical path. This analyzer 21 is adapted to transmit only a polarizing composition of light reflected from the polarized beam splitter 6. Accordingly, the reflecting light from the eye fundus $E_f$ is guided to the opposite way with respect to the illuminating light along the same optical path from the polarized beam splitter 6 to the half mirror 18 of the illuminating system and thereafter, made incident to the photomultiplier 19 through the analyzer 21, the condenser lens 22, and the pin hole 23.

The second light receiving system uses the same optical path from the dichroic mirror 7 to the half mirror 18 of the illuminating system and further comprises an interference filter 24, a condenser lens 25, a pin hole 26, etc. in addition to this optical path. The interference filter 24 is adapted to transmit only a fluorescent wavelength of 520 nm reflected by the dichroic mirror 7. Accordingly, the fluorescence from the blood vessel of the eye fundus $E_f$ is guided to the opposite way with respect to the illuminating light along the same optical path from the dichroic mirror 7 to the half mirror 18 of the illuminating system and made incident to the photomultiplier 20 through the interference filter 24, the condenser lens 25, and the pin hole 26.

The eye fundus camera includes a first field photoelectric element 27, as a first irradiating light receiving portion, for detecting a light quantity level of the illuminating light (laser beam) at the end portion of the laser beam generator 1 side of the illuminating system, and a second field photoelectric element 28, as a second irradiating light receiving portion, for detecting the light quantity level of the illuminating light which is irradiated from the illuminating system toward the eye E. Moreover, a part of the laser beam of the illuminating system is guided to the photoelectric element 27 through the half mirror 5 and the condenser lens 29, whereas the laser beam outgoing from the illuminating system is guided to the photoelectric element 28 through the half mirror 18 and the condenser lens 30.

An electronic circuit which cooperates with such optical system and the function thereof will now be described.

The X-scanner 8 includes, in addition to the polygon mirror 8a, a motor 8b for driving the polygon mirror 8a, a driver (not shown) for actuating the motor 8b, a control circuit (not shown) for controlling the driver, a turning position detecting means (not shown) for detecting the turning position of the polygon mirror 8a, 1 horizontal scanning start signal generating circuit (not shown) for outputting 1 horizontal scanning start signal upon receipt of a signal from the turning position detecting means, etc. The X-scanner 8 is adapted to scan a laser beam in the horizontal direction by turning the polygon mirror 8a.

The Y-scanner includes, in addition to the galvano mirror 16a, a driver (not shown) for driving the galvano mirror 16a, a control circuit (not shown) for controlling the driver, position detecting means (not shown) for detecting the initial position of the galvano mirror 16a, etc. And, the control circuit of the Y-scanner 16, upon receipt of 1 horizontal scanning start signal from the X-scanner 8, generates a dot clock which is in synchronism therewith and actuates the driver of the galvano mirror 16a after a predetermined dot scanning is over, so that the galvano mirror 16a is turned at predetermined angles for gradually changing the horizontal scanning position. The control circuit of the Y-scanner 16, when the galvano mirror 16a has been turned predetermined times by the driver, outputs 1 frame scanning complete signal to return the Y-scanner 16 to the start position.

Such 1 horizontal scanning start signal from the X-scanner 8 and such 1 frame scanning complete signal from the Y-scanner 16 are input into an address circuit 31.

On the other hand, the photomultiplier 19 is input with a reflecting light from the eye fundus $E_f$ through the first light receiving system, whereas the photomultiplier 20 is input with fluorescence from the blood vessel of the eye fundus $E_f$ through the second light receiving system. Similarly, the photoelectric element 27 is input with a part of a laser beam at the end portion of the laser beam generator 1 side of the illuminating system at that time, whereas the photoelectric element 28 is input with a part of an outgoing light of the laser beam of the illuminating system. And, an output signal of the photomultiplier 19 is amplified by an amplifier 32 and, thereafter, input into an A/D converter 33, whereas an output signal of the photomultiplier 20 is amplified by an amplifier 34 and, thereafter, input into an A/D converter 35. The output signals of the photoelectric elements 27, 28 are input into a correction control circuit 36. The output signals of the photoelectric elements 27, 28 always maintain a constant ratio when the lenses, mirrors, etc. of the illuminating system are free of dirt or dust. However, the ratio is changed when the lenses, mirrors, etc. of the illuminating system are clouded with dirt or dust. Therefore, if the ratio shows any change, it is known from the change that the lenses, mirrors, etc. of the illuminating system are clouded with dirt or dust. Therefore, the correction control circuit 36 controls the amplifiers 32, 34 in accordance with the change of the ratio and corrects the quantity of output signals of the photomultipliers 19, 20 to a level which can be obtained when a laser beam scans the eye fundus $E_f$ in the state that the reduction of the light quantity due to dirt, dust or the like does not take place. Moreover, the irregularity of the light emitting quantity of the laser beam generator 1 itself can be detected and corrected simultaneously only by the output signal of the photoelectric element 27.

In this way, the analog signals amplified by the amplifiers 32, 34 are converted to digital signals by the A/D converters 33, 35.

The output from the A/D converter 33 is input into a first memory 38 or a second memory 39 as an ordinary eye fundus image memory through a switch 37, whereas the output of the first memory 38 or the second memory 39 is input into a D/A converter 41 through a switch 40. Similarly, the output of the D/A converter 41 is input into a first video signal generating circuit 42. A part of the output of the video signal generating circuit 42 is input into the first memory 38 or the second memory 39 through a memory access circuit 43 or a switch 44. The output of the video signal generating circuit 42 is input into a first VTR 45 and also input into a monitor TV 47 through an image composing device 46.

Likewise, the output from the A/D converter 35 is input into a third memory 49 or a fourth memory 50 as a fluorescent eye fundus image memory through a switch 48, whereas the output of the third memory 49 or the fourth memory 50 is input into a D/A converter 52 through a switch 51. Similarly, the output of the D/A converter 52 is input into a second video signal generating circuit 53. A part of the output of the video signal generating circuit 53 is input into the third memory 49 or the fourth memory 50 through a memory access circuit 54 or a switch 55. The output of the video signal generating circuit 53 is input into a second VTR 56 and also input into the monitor TV 47 through the image composing device 46. The output of the VTR 56 is also input into the monitor TV 47 through the image composing device 46. The image composing device 46 can separately send the signals from the video signal generating circuits 42, 53 to the TV monitor TV 47. The image composing device 46 can compose the signals from the video signal generating circuits 42, 53 according to necessity and then send to the monitor TV 47.

The address signal of the address circuit 31 is input into the first memory 38 or the second memory 39 through a switch 57 and also input into the third memory 49 or the fourth memory 50 through a switch 58. The switches 37, 40, 44, 48, 51, 55, 57 and 58 can be switched by 1 frame scanning complete signal from the Y-scanner 16.

At that time, the switches 37, 40 and 57 can be switched in the following manner. That is, when the digital signals from the A/D converter 33 are being memorized in a predetermined address of either first memory 38 or second memory 39 one after another by the switches 37, 57, the memory access circuit 43 accesses one frame portion of signals memorized in the remaining first memory 38 or second memory 39 through the switch 44, and the accessed signals are input into the D/A converter 43 by the switch 40. Specifically, when the signals are being memorized in the first memory 38, the monitor TV 47 reproduces the image in accordance with the one frame portion of signals memorized in the second memory 39, whereas when the signals are being memorized in the second memory 39, the monitor TV 47 reproduces the image in accordance with the one frame portion of signals memorized in the first memory 38. By following the foregoing procedures, a stable image of the eye fundus $E_f$ can be reproduced on the monitor TV 47, even if the scanning speed of the eye fundus $E_f$ by laser beam and the signal processing speed by the video signal generating circuit 43 are greatly different.

Similarly, the switches 48, 51, 55 and 58 can be switched in the following manner. That is, when the digital signals from the A/D converter 35 are being memorized in a predetermined address of either third memory 49 or fourth memory 50 one after another by the switches 48, 58, the memory access circuit 54 accesses one frame portion of signals memorized in the remaining third memory 49 or fourth memory 50 through the switch 55, and the accessed signals are input into the D/A converter 52 by the switch 51. Specifically, when the signals are being memorized in the third memory 49, the monitor TV 47 reproduces the image in accordance with the one frame portion of signals memorized in the fourth memory 50, whereas when the signals are being memorized in the fourth memory 50, the monitor TV 47 reproduces the image in accordance with the one frame portion of signals memorized in the third memory 49. By following the foregoing procedures, a stable image of the eye fundus $E_f$ can be reproduced on the monitor TV 47, even if the scanning speed of the eye fundus $E_f$ by laser beam and the signal processing speed by the video signal generating circuit 43 are greatly different.

Therefore, the illuminating system irradiates the laser beam from the laser beam generator 1 toward the eye E to scan the eye fundus $E_f$ by the X-scanner 8 and the Y-scanner 16. By this scanning, the laser beam reflected by the eye fundus $E_f$ is input into the photomultiplier 19 through the first light receiving system and memorized one frame by one frame as a digital signal in the first memory 38 or the second memory 39 as described. And, the signal memorized in the first memory 38 or the second memory 39 is alternately accessed and input into the VTR 45 through the D/A converter 41 and the video signal generating circuit 42. Moreover, the output from the video signal generating circuit 42 is input into the monitor TV 47 through the image composing device 46 and can be observed on the monitor TV 47.

On the other hand, if a fluorescent picture taking is undergoing at that time, the fluorescent agent in the blood vessel of the eye fundus $E_f$ is excited by the laser beam and emits fluorescence. This fluorescence is received by the photomultiplier 20 through the second light receiving system and memorized one frame by one frame as a digital signal in the third memory 49 or the fourth memory 50 as described. And, the signal memorized in the third memory 49 or the fourth memory 50 is alternately accessed and input into the VTR 56 through the D/A converter 52 and the video signal generating circuit 53. Moreover, the output from the video signal generating circuit 53 is input into the monitor TV 47 through the image composing device 46 and can be observed on the monitor TV 47.

The output from the video signal generating circuits 42, 53 is composed by the image composing device 46 and then input into the monitor TV 47, so that they can be observed on the monitor TV 47 in their overlapped state.

In this way, according to the present invention, since a picture-taking of the blood vessel of the eye fundus by fluorescence and a picture-taking of the eye fundus $E_f$ can be carried out simultaneously, the focussing of the eye fundus camera can be effected by the ordinary observation picturetaking procedure from before the appearance of the blood vessel image of the eye fundus by fluorescence until the end of the procedure. Moreover, since the blood vessel image of the eye fundus and the eye fundus image by fluorescence can be composed by the image composing device 46 and observed them in the overlapped state on one monitor TV simultaneously, the positional relationship between the blood vessel image of the eye fundus and the eye fundus image can be obtained correctly.

FIG. 7 illustrates the second embodiment of the present invention.

This embodiment shows one example of an optical system which can be used whether the laser beam is a randam beam or a linearly polarized beam.

In this embodiment, the polarized beam splitter 6 is replaced with a half mirror 59, and a polarizer 60 and a quarter-wave plate 61 are interposed in this order between the half mirrors 5, 8 and the dichroic mirror 7. Accordingly, the linearly polarized laser beam is polarized into a circularly polarized laser beam by the quarter-wave plate 61 and then irradiated to the eye E.

FIG. 8 illustrates one example of an optical system in which the laser beam generated from the laser beam generator 1 is a linearly polarized laser beam.

In this embodiment, since the laser beam generated from the laser beam generator 1 is linearly polarized, the polarized beam splitter 6 may merely replaced with a half mirror 62.

As described in the foregoing, according to the present invention, since the observation picture-taking of the blood vessel of the eye fundus by fluorescence and the ordinary observation picture-taking of the eye fundus can be effected simultaneously, when the blood vessel of the eye fundus is to be taken a picture by fluorescence, the focussing of the eye fundus camera can be easily effected by observing the eye fundus image according to the ordinary manner until the fluorescence of the blood vessel of the eye fundus appears. Therefore, a correct observation by fluorescence can be obtained.

Moreover, since the observation picture-taking of the blood vessel of the eye fundus by fluorescence and the ordinary method of the eye fundus can be carried out simultaneously, two images obtained by these two observation picture-takings are not displaced with each other, and the images can be correctly observed in the overlapped state when both the images are to be reproduced according to necessity.

What is claimed is:

1. A laser beam scanning type eye fundus camera, for observing and photographing an eye fundus having blood vessels capable of carrying a fluorescent substance, the eye fundus camera comprising:
   a laser beam generator for generating a laser beam;
   an illuminating system for illuminating the fundus of an eye to be tested by scanning the laser beam generated by said laser beam generator on the eye fundus;
   first and second light receiving portions for receiving a reflecting light of the laser beam reflected by the eye fundus and generating first and second light intensity signals, respectively, in response thereto;
   a first light receiving system for guiding the reflecting light of the laser beam reflected by the eye fundus to said first light receiving portion;
   a second light receiving system for guiding fluorescence excited radiation generated by exciting a fluorescent substance in the eye fundus blood vessels with the laser beam to the second light receiving portion; and
   an electronic circuit for forming an eye fundus image on a monitor TV according to an output signal coming from said first and second light receiving portions.

2. A laser beam scanning type eye fundus camera according to claim 1, which further includes:
   a first photoelectric element for detecting the intensity of the laser beam emitted by the laser beam generator and generating a first laser intensity signal in response thereto;
   a second photoelectric element for detecting the intensity of the laser beam emanating from said illuminating system and generating a second laser intensity signal in response thereto; and
   a correction controlling circuit for comparing the ratio of said first and second laser intensity signals and generating a correction signal in response thereto.

3. A laser scanning type eye fundus camera according to claim 1, wherein said electronic circuit includes an ordinary eye fundus image memory for memorizing one frame portion of signal for a video signal in accordance with output from said first light receiving portion; a first video signal generating circuit for generating a video signal in accordance with a signal from said ordinary eye fundus image memory; a fluorescent eye fundus image memory for memorizing one frame portion of signal for a video signal in accordance with output from said second light receiving portion; and a second video signal generating circuit for generating a video signal in accordance with a signal from said fluorescent eye fundus image memory.

4. A laser beam scanning type eye fundus camera according to claim 3, wherein said ordinary eye fundus image memory comprises a first and a second memories which are alternately operated for each frame of the film, and said fluorescent eye fundus image memory comprises a first and a second memories which are alternately operated for each frame of the film.

5. A laser beam scanning type eye fundus camera according to claim 3 or claim 4, wherein the video signal output from said first and second video signal generating circuits can be input into a first and a second VTRs respectively, and the video signals output by said first and second video signal generating circuits and the video signals output by said first and second VTRs can be input into said monitor TV.

6. A laser beam scanning type eye fundus camera according to claim 5, wherein the video signals output by said first and second video signal generating circuits and the video signals output by said first and second VTRs can be input into said monitor TV through an image composing device.

7. A laser beam scanning type eye fundus camera according to claim 1, wherein said illuminating system includes means for changing the diameter of laser beam.

8. A laser beam scanning type eye fundus camera according to claim 7, wherein said beam diameter changing means is a variable lens for changing the angle of view.

9. A laser beam scanning type eye fundus camera, comprising:
   a laser beam generator for generating a laser beam;
   an illuminating system for illuminating the fundus of an eye to be tested by scanning the laser beam generated by said laser beam generator on the eye fundus;
   a light receiving portion for receiving a reflecting light reflected by said eye fundus and generating a light intensity signal in response thereto;
   a light receiving system for guiding the reflecting light of the laser beam reflected by the eye fundus to said light receiving portion;
   an electronic circuit for forming an eye fundus image on a monitor TV in accordance with an output signal from said light receiving portion;
   a first photoelectric element for detecting the intensity of the laser beam emitted by the laser beam generator and generating a first laser intensity signal in response thertо;
   a second photoelectric element for detecting the intensity of the laser beam emanating from said illuminating system and generating a second laser intensity signal in response thereto; and
   a correction controlling circuit for comparing the ratio of said first and second laser intensity signals and generating a correction signal in response thereto.

10. A laser beam scanning type eye fundus camera according to claim 1, further including first and second amplifier means to amplify said first and second light intensity signals, said first and second amplifier means changing the amplification of said first and second light intensity signals in response to said correction signal to maintain the ratio of said first and second light intensity signals at a desired level.

11. A laser beam scanning type eye fundus camera according to claim 9, further including amplifier means to amplify said light intensity signal, said amplifier means changing the amplification of said light intensity signal in response to said correction signal to maintain said light intensity signal at a desired level.

12. A laser beam scanning type eye fundus camera comprising:
   a laser beam generator for generating a laser of a wavelength capable of generating fluorescence radiation from a fluorescent material circulating in a blood vessel of an eye fundus of a person to be tested by exciting the material;

an illuminating system for scanning and illuminating said eye fundus with a laser beam coming from said laser beam generator;

a first light receiving system for guiding a laser beam reflected by said eye fundus to a first light receiving portion;

a second light receiving system for guiding fluorescence radiation generated when said fluorescent material circulating in a blood vessel of said eye fundus is excited by said laser beam to a second light receiving portion, said fluorescence radiation being of a different wavelength from that of said laser beam; and an electronic circuit for forming an eye fundus image on a TV monitor in response to output signals coming from said first and second light receiving portions.

13. A laser beam scanning type eye fundus camera according to claim 1, which further includes a first photoelectric element for detecting the level of the quantity of a laser beam at an end portion of the laser beam generator side of said illuminating system, a second photoelectric element for detecting the level of the quantity of a laser beam at the eye side of said illuminating system; and a circuit for correcting the level of the output signals from said first and second light receiving portions in accordance with a charge in a ratio of output of said second photoelectric element with respect to output of said first photoelectric element to levels of output signals from said first and second light receiving portions extant before said change in said ratio.

14. A laser beam scanning type eye fundus camera including a laser beam generator for generating a laser beam:

an illuminating light system for scanning and illuminating an eye fundus of an eye to be tested with a laser beam coming from said laser beam generator;

a light receiving system for guiding a light coming from said eye fundus due to said scanning and illuminating of said eye fundus with said laser beam to a light receiving portion; and a first photoelectric element for detecting the level of the quantity of a laser beam at an end portion of the laser beam generator side of said illuminating system, a second photoelectric element for detecting the level of the quantity of a laser beam at the eye side of said illuminating system; and a circuit for correcting the level of the output signals from said light receiving portion in accordance with a change in a ratio of output of said second photoelectric element with respect to output of said first photoelectric element to levels of output signals from said receiving portion extant before said change in said ratio.

15. A laser beam scanning type eye fundus camera according to claim 12, wherein said illuminating system includes diameter changing means, said diameter changing means including a variable lens for changing the angle of view.

* * * * *